United States Patent
Chow et al.

(10) Patent No.: US 6,518,997 B1
(45) Date of Patent: Feb. 11, 2003

(54) GRID ARRAY INSPECTION SYSTEM AND METHOD

(75) Inventors: Hon Yean Chow, Singapore (SG); De Yong Luo, Singapore (SG); Jia Ju Li, Singapore (SG)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 09/130,197

(22) Filed: Aug. 5, 1998

(51) Int. Cl.⁷ .................................................. H04N 7/18
(52) U.S. Cl. ...................................................... 348/126
(58) Field of Search ...................... 250/559.23; 348/125, 348/126, 86, 87, 92–95, 129–131; 356/3.01, 4.04, 602, 608; 359/629, 633, 639, 368; 382/145–151; H04N 7/18

(56) References Cited

U.S. PATENT DOCUMENTS

| | | | | |
|---|---|---|---|---|
| 5,024,569 A | * | 6/1991 | Svetkoff et al. | 346/606 |
| 5,028,799 A | * | 7/1991 | Chen et al. | 356/602 |
| 5,162,866 A | | 11/1992 | Tomiya, et al. | |
| 5,212,390 A | | 5/1993 | Le Beau, et al. | |
| 5,450,206 A | | 9/1995 | Caillat, et al. | |
| 5,465,152 A | | 11/1995 | Bilodeau, et al. | |
| 5,621,530 A | | 4/1997 | Marrable, Jr. | |
| 5,652,658 A | | 7/1997 | Jackson, et al. | |
| 5,734,507 A | * | 3/1998 | Harvey | 359/639 |
| 5,790,242 A | * | 8/1998 | Stern et al. | 356/4.04 |
| 5,812,268 A | * | 9/1998 | Jackson et al. | 348/126 |
| 5,812,269 A | * | 9/1998 | Svetkoff et al. | 356/602 |
| 5,815,275 A | * | 9/1998 | Svetkoff et al. | 346/608 |
| 5,903,662 A | * | 5/1999 | DeCarlo | 382/145 |
| 5,995,220 A | * | 11/1999 | Suzuki | 348/126 |
| 6,025,905 A | * | 2/2000 | Sussman | 356/3.01 |
| 6,072,898 A | * | 6/2000 | Beaty et al. | 382/146 |
| 6,118,524 A | * | 9/2000 | King et al. | 348/126 |
| 6,118,540 A | * | 9/2000 | Roy et al. | 348/126 |
| 6,201,639 B1 | * | 3/2001 | Overbeck | 359/368 |

* cited by examiner

*Primary Examiner*—Richard Lee
(74) *Attorney, Agent, or Firm*—Beyer Weaver & Thomas, LLP

(57) ABSTRACT

An inspection apparatus and method is provided for inspecting external lead connectors in a grid array of an electronic package. The inspection apparatus includes a plurality of reflecting devices for directing a plurality of different oblique images to a partially reflective beam splitter, wherein each of the plurality of images corresponds to a different perspective view of the grid array. The apparatus is further configured such that each of the plurality of images share a single, common X,Y coordinate system for describing point locations within each image. An image capturing device captures each oblique image from the beam splitter. By comparing the relative location of image points in at least two captured images, the spatial coordinates and physical parameters of each solder ball may be calculated. The calculated values are converted to absolute values and compared against predetermined values for determining whether the electronic package meets manufacturing standards.

61 Claims, 4 Drawing Sheets

GRID ARRAY INSPECTION SYSTEM AND METHOD

BACKGROUND OF THE INVENTION

Surface mount technology has made it possible to densely populate both sides of a circuit board with semiconductor devices. Because leads of a surface mount integrated circuit (IC) package may be placed closer together than through-hole pins of a dual-in-line package (DIP), the component size of surface mount ICs has correspondingly decreased. These small packages have been termed small-outline IC packages and chip carriers. Chip carriers are typically used in applications that require large lead counts and employ a variety of mounting techniques such as, flat packs, quad flat packs (QFP), J-leads, Gull-wing leads, leadless, and the more recent development of ball grid arrays (BGAs).

The ball grid array mounting technique uses rows and columns of closely positioned solder balls located on one side of the package as the outer leads of the integrated circuit. Ball grid array packages offer many advantages including lower yield loss from bent leads and misregistration, higher throughput from greater placement tolerances and a more repeatable assembly process. However, a major concern with the ball grid array package is non-uniformity of the solder balls which may translate to defective solder joints. It is of extreme importance, therefore, to inspect and verify the physical parameters of each ball in the ball grid array to insure that the parameters fall within manufacturing specifications. However, because the solder balls are arranged in rows and columns, the profiles of the solder balls located behind the outer rows and columns are not easily inspected.

The importance of visual mechanical inspection for BGA devices is well appreciated in the art. Various inspection systems and apparatus are currently used in the manufacturing industry, such as, for example, those found and described in U.S. Pat. Nos. 5,162,866; 5,212,390; 5,450,206; 5,465,152; 5,652,658; and 5,621,530. However, conventional lead inspection techniques suffer from a variety of drawbacks relating to size constraints, power consumption, cost, and reliability of the inspection system. For example, some lead inspection systems employ an optical beam which scans across the grid array to verify the physical parameters of each connector in the array. The use of moving parts in such systems, however, increases size requirements of the inspecting device, and reduces reliability.

What is desired is a lead inspection system which can reliably inspect the pertinent parameters of a grid array package. It is also desirable to provide a lead inspection apparatus which is simple in design, and space efficient. It is an object of the present invention, therefore, to provide a lead inspection system which is space efficient and simple in design, and which can be constructed into a compact inspection module for in-process application. It is yet another object of the present invention to provide a lead inspection apparatus which attains a high inspection speed. It is a further object of the present invention to provide a lead inspection system which reliably inspects the pertinent parameters of a grid array and which minimizes the use of moving parts.

SUMMARY OF THE INVENTION

These and additional objects are accomplished by the various aspects of the present invention wherein, briefly, according to a principal aspect, an inspection technique is provided which makes use of machine vision in conjunction with a customized optical system to capture different oblique images of the grid array. The captured images are analyzed and used for computation of the pertinent parameters required for inspection analysis.

Accordingly, a first aspect of the present invention is directed to an inspection apparatus for an electronic package having a grid array of connectors mounted on a substrate. The inspection apparatus includes an image capturing device and an image providing means for providing a plurality of images of the grid array to the image capturing device, wherein each of the plurality of images corresponds to a different perspective view of the grid array. Furthermore, each of the plurality of images which are captured by the image capturing device are mappable to a single coordinate system. By using a single coordinate system to compare the relative locations of solder balls in each of the captured images, the spatial coordinates and physical parameters of each solder ball may be calculated.

A second aspect of the present invention is directed to an inspection apparatus for an electronic package having a grid array of connectors mounted on a substrate. The apparatus comprises an image capturing device; a beam splitter; and at least two image reflecting devices, positioned on either side of the beam splitter for directing a first oblique image and a second oblique image of the grid array to the image capturing device. More specifically, a first reflecting device directs a first image of the grid array to the beam splitter, the first image corresponding to a first perspective view of the grid array. A second reflecting device directs a second image of the grid array to the beam splitter, the second image corresponding to a second perspective view of the grid array which is different from that of the first perspective view. The image capturing device captures the first and second oblique image from the beam splitter. The first and second captured images are directly mappable to a single coordinate system, and are used by the apparatus to compute the spatial coordinates and physical parameters of each solder ball in the grid array.

A third aspect of the present invention is directed to an inspection apparatus for an electronic package having a grid array of connectors mounted on a substrate. The apparatus comprises a plurality of image capturing devices, including a first image capturing device an a second image capturing device. The first image capturing device is positioned to capture a first oblique image of the grid array form a first perspective, and the second image capturing device is positioned to capture a second oblique image of the grid array from a second perspective which is different than that of the first perspective. The apparatus further includes converting means for converting the first image and second image to respective images which are both mappable to a single coordinate system. The apparatus further includes calculating means adapted to receive each of the converted images from the converting means for using at least two of a plurality of captured images to calculate the spatial coordinate values of each connector of the grid array.

A fourth aspect of the present invention is directed to a method for computing spatial coordinate values of each connector in the grid array of an electronic package. The method comprises the steps of providing to an image capturing device a first oblique image of the grid array and a second oblique image of the grid array; assigning to the first and second image a common X, Y coordinate system for describing relative positions of image points within each respective first and second image. The method further includes the step of using the X, Y coordinate values of the respective first and second image points to compute representative spatial coordinates X, Y, Z of each connector of the grid array.

A fifth aspect of the present invention is directed to a method for inspecting an array of external lead connectors mounted on a substrate of an electronic package. The method comprises these steps of providing a plurality of images of the grid array to an image capturing device, wherein each of the plurality of images corresponds to a different perspective view of the grid array, and wherein each of the plurality of images is mappable to a single coordinate system; using at least two of the plurality of captured images to calculate spatial coordinate values of each connector of the grid array; and comparing the calculating spatial coordinate values with predetermined values to determine whether the electronic package meets acceptable manufacturing standards.

A sixth aspect of the present invention is directed to a method for inspecting an array of external lead connectors mounted on a substrate of an electronic package. The method comprises the steps of providing to an image capturing device a first oblique image of the grid array and a second oblique image of the grid array; mapping the first and second images to a X, Y coordinate system; using X, Y coordinate values of image points within the first and second images to compute representative spatial coordinates (X, Y, Z) of each connector of the grid array; and comparing the computed spatial coordinate values with predetermined values to determine whether the electronic package meets acceptable manufacturing standards.

By using the technique of the present invention, lead inspection of electronic packages may be performed without moving parts, thereby increasing the reliability of the inspection technique. Furthermore, the inspection system of the present invention is able to be constructed into a compact inspection module for in-process applications, and requires less space than that of conventional inspection systems. Additionally, the inspection system of the present invention is simple in design and is less costly than many conventional lead inspection systems.

Additional objects, features and advantages of the various aspects of the present invention will become apparent from the following description of its preferred embodiments, which description should be taken in conjunction with the accompanying drawings.

DETAILED DESCRIPTION OF THE PREFERRED EMBODIMENT

Figure 1:
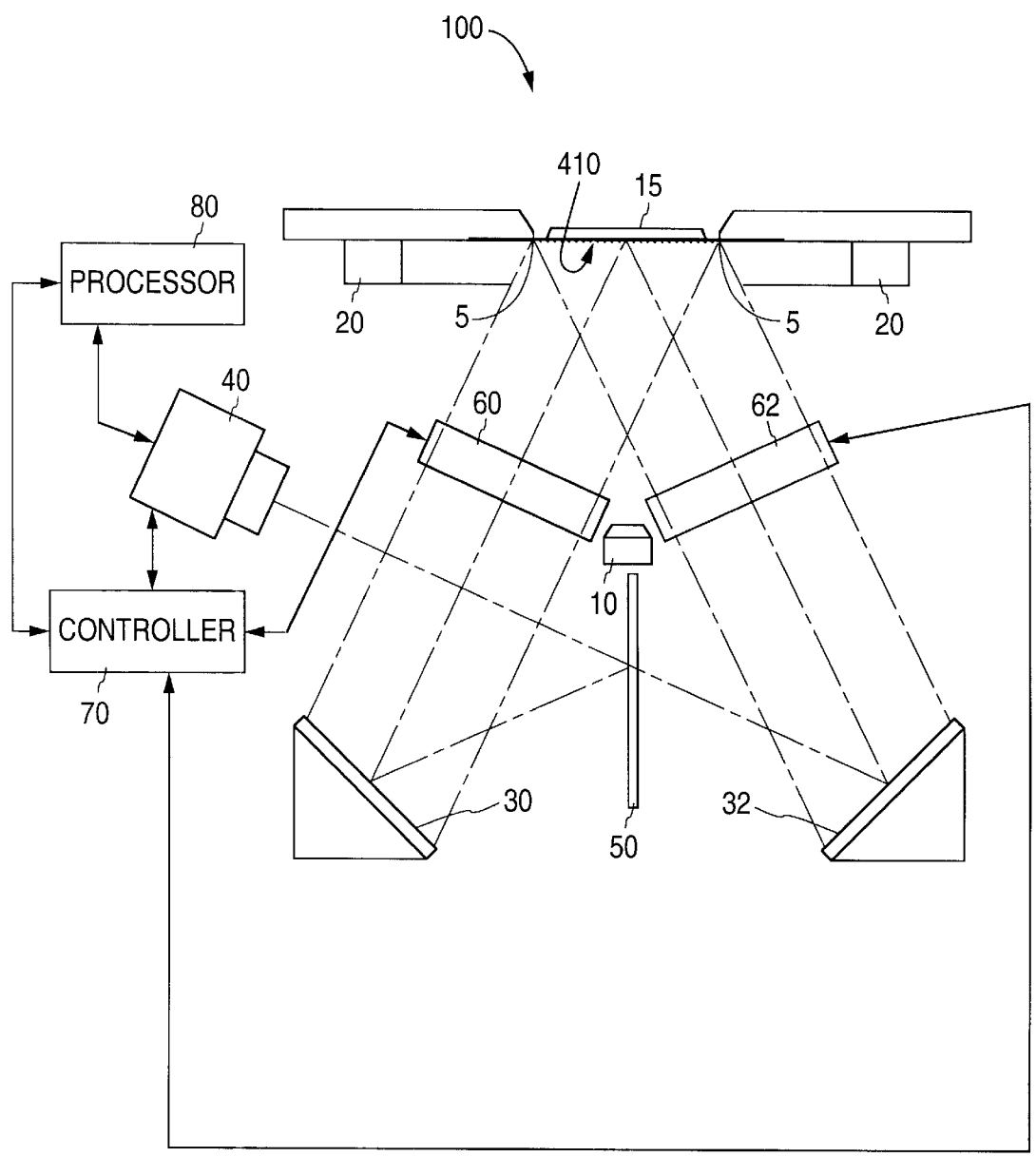
FIG. 1 is a schematic diagram illustrating one embodiment of the inspection apparatus of the present invention.
Figure 4:
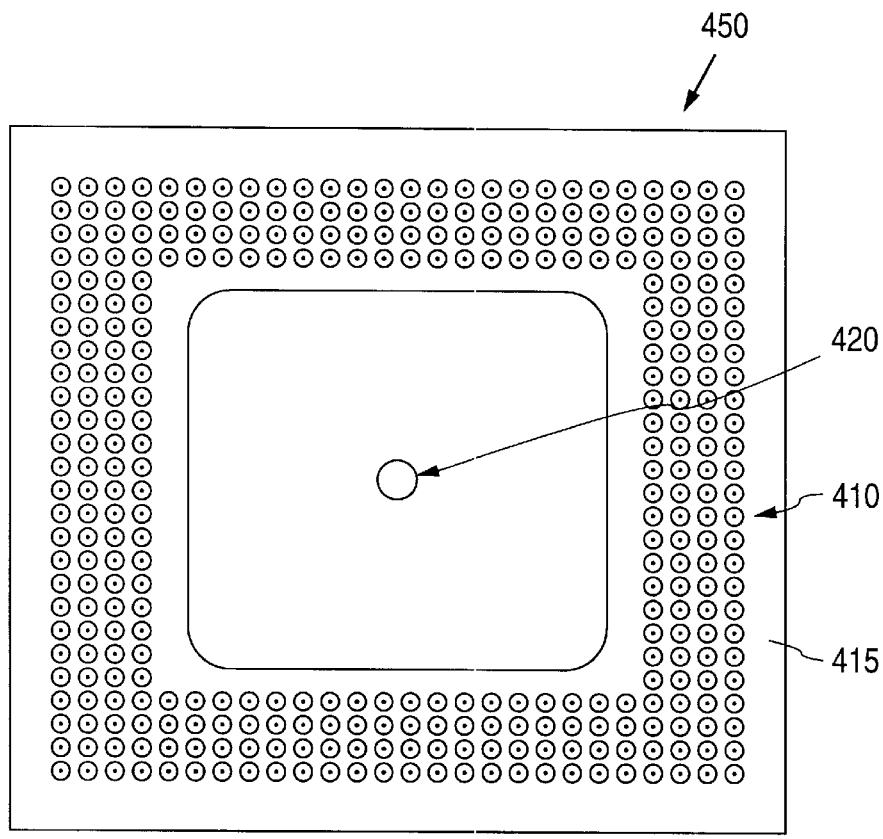
FIG. 4 shows an actual captured images of one type of ball grid array, showing the plurality of external lead connectors 410 and centered laser reference point 420.

FIG. 1 illustrates a schematic diagram of one embodiment of the lead inspection system 100 of the present invention. As illustrated in FIG. 1, a ball grid array package 15 sits in an orifice which is supported by thin steel stoppers 5. The bottom of the BGA package contains a plurality of solder ball connectors 410, otherwise referred to as a ball grid array. The BGA package 15 is oriented in the live bug position. The BGA package 15 is illuminated by a ringed light source 20, which is mounted immediately below the package 15, as shown in FIG. 1. One advantage of using a ringed light source to illuminate the grid array is that, due to the reflective nature of the solder balls in the grid array, the distal end portions (or tips) of each solder ball in the grid array can be easily identified, as shown, for example, in FIGS. 4 and 5 of the drawings. Thus, as shown in FIG. 4, for example, each solder ball can be seen comprising a white ring with a black center. This center point indicates the distal end portion (or tip portion) of the solder ball. Thus, using a ringed light source, the inspection and measurement process of the physical parameters of each solder ball is facilitated.

Referring back to FIG. 1, two reflecting devices 30 and 32 are positioned relative to the grid array 410 such that the first reflecting device 30 is able to provide a different perspective view of the grid array than reflecting device 32. Although not shown in the drawings, other reflecting devices may be included in the inspection system for providing alternate perspective views of grid array 410 which differ from those of reflecting devices 30 and 32. In the embodiment show in FIG. 1, reflecting devices 30 and 32 are inclined mirrors. However, other reflecting devices may also be used in the inspection system of the present invention such as, for example, prisms, or other reflective devices commonly known to those skilled in the art.

In the embodiment of FIG. 1, a left oblique image of the grid array 410 is reflected by mirror 30 to beam splitter 50. Beam splitter plate 50 includes a partially reflective surface so that images may either be reflected from the surface of beam splitter 50 or pass through the body of beam splitter 50 to the image capturing device 40. The light ray of the left oblique image leaving mirror 30 is reflected by the beam splitter 50 to an image capturing device 40. The image capturing device 40 may be, for example, a CCD camera, or other suitable image capturing device, which, preferably captures the image from the beam splitter in digital form. A right oblique image of the grid array 410 is reflected by mirror 32 to beam splitter 50. The light ray which is reflected from mirror 32 to beam splitter 50 passes through the beam splitter and onto the image capturing device 40.

The inspection system of the present invention includes a high resolution CCD camera 40, which captures images of the grid array from beam splitter 50, and provides these images to processor unit 80. In the embodiment of FIG. 1, left and right oblique images of grid array 410 are captured by camera 40. It is to be understood, however, that other images corresponding to different perspective views of grid array 410 may also be captured by camera 40 and provided to processor 80 for analysis. The digitized image data from each image captured by camera 40 is sent to processor 80 and stored in a memory buffer of a computer vision frame grabber for digital image processing. As explained in greater detail below, the left and right oblique images provided by mirrors 30 and 32 are aligned by design to superimpose on a beam splitter plate 50 for image capture by the CCD camera 40. A single, superimposed image of the two oblique views of the grid array may be captured by the CCD camera for processing and parameter computation. However, it is preferable to capture each of the plurality of oblique images separately as this simplifies the digital image processing. In order to enable dual image capture by one fixed CCD camera, two electric light shutter 60 and 62 are introduced as shown in FIG. 1.

As shown in FIG. 1, a plurality of reflective devices 30, 32 simultaneously provide respectively different perspective views of the grid array 410 to beam splitter plate 50. In order for the CCD camera 40 to capture individual images from the beam splitter 50, a plurality of electronic light shutters 60, 62 are used in a coordinated arrangement to block the light paths of each image of the plurality of images except for a selected image which is provided to the image capturing device. Thus, in the embodiment shown in FIG. 1, two light shutters 60, 62 are used to selectively choose either the right or the left oblique image of the grid array to be passed to the image capturing device 40. Generally speaking, however, one electronic light shutter is preferably used for each perspective view or oblique image which is provided to the image capturing device.

As shown in FIG. 1, each electronic light shutter 60, 62 is connected to a controller unit 70 which controls the state, either open or closed, of each shutter device. To enable the camera 40 to capture a selected image of the grid array, for example, the left oblique image provided by mirror 30, the controller unit 70 configures shutter 60 to be open, and shutter 62 to be closed simultaneously during the frame grabbing cycle or frame capturing cycle by camera 40. In the same manner, for capturing the right oblique image from mirror 32, the controller configures shutter 62 to be open and shutter 60 to be closed simultaneously so that the right oblique image of the grid array reflects from mirror 32 through the beam splitter 50 and is captured by camera 40. In alternate embodiments where more than two oblique images are provided to the image capturing device 40, a plurality of electronic light shutters may be provided, with one shutter corresponding to each associated oblique image. The controller circuit 70 may coordinate the operation of the plurality of light shutters to enable a selected one of a plurality of images to be provided to the camera 40 at a given time for capturing. Additionally, although not shown in the drawings, the physical location of each shutter within the inspection system 100 of the present invention may be modified. For example, electronic shutter 60 may be interposed between mirror 30 and beam splitter 50. Similarly, electronic light shutter 62 may be interposed between mirror 32 and beam splitter 50. It is important that each shutter device be positioned so as to effectively cut out or block its corresponding oblique image of the grid array if desired. Additionally, it is important that the position of each shutter device be such that it does not interfere with the other images which are to be captured by camera 40.

Referring back to FIG. 1, while both electronic light shutters are open, camera 40 views a superimposed right and left oblique image of grid array 410. However, it is preferable that each individual oblique image be captured separately, wherein the digital image data of each image can then be used to compute the pertinent spatial coordinates X, Y and Z of each solder ball of the grid array.

In the optical system setup of the present invention, there exists a unique optical reference plane running parallel through the beam splitter 50 to intersect perpendicularly the base of the BGA package 15, which is positioned at a fixed distance away from the beam splitter and its two associated inclined mirrors. Camera 40 is fixed with its axis inclined to the beam splitter 50 to view the superimposed oblique images. This forms the optical system of the inspection apparatus of the present invention. The optical system is aligned so that a focus point in the center of the base of the BGA device, on the unique optical reference plane, forms a corresponding image in the center of the beam splitter plate 50 for camera viewing. This focus point serves as a reference point for solder ball height measurement calculations performed by the inspection system of the present invention. The horizontal plane running through this reference point functions as a reference plane for solder ball height measurement. The spatial coordinates of the dark spots of each solder ball (representing the tip points or distal end portions of each solder ball) in the grid array are measured as described in later sections.

In addition to the spatial coordinate measurements of the distal end portions of the connectors in the grid array, a small laser target spot may be focused onto a selected point of the ball grid array base (or substrate portion of the BGA package) to enable spatial coordinate measurement of the selected point. By way of illustration, FIG. 4 illustrates laser reference point 420, which illuminates the center portion of the BGA substrate.

FIG. 1 illustrates laser assembly unit 10, which is positioned to project a laser spot on a portion of the base of the BGA package. The laser assembly unit 10 may include a self-focusing laser diode device, for example, or other type of laser device which would be suitable for projecting a targeted laser spot on a desired portion of the base of the BGA package. The self-focusing laser diode assembly 10 is included to target a focused laser spot or reference point onto any dark portion of the base of the semiconductor package. The illuminated reference point may be used to calculate the spatial coordinates X, Y, and Z of that point using the technique of the present invention. Thus, by using laser assembly 10, the spatial coordinates of any desired point of the package may be determined.

Using the technique of the present invention, the spatial coordinates X,Y,Z of any illuminated grid array point and the center of a small targeted laser spot may be determined. The calculated values of the pertinent parameters for the spatial coordinates of the grid array connectors and laser reference point are then converted to absolute length readings using correction factors obtained by, for example, correlating with measurements made on prior calibrated units or specially designed calibrators.

Figure 2:
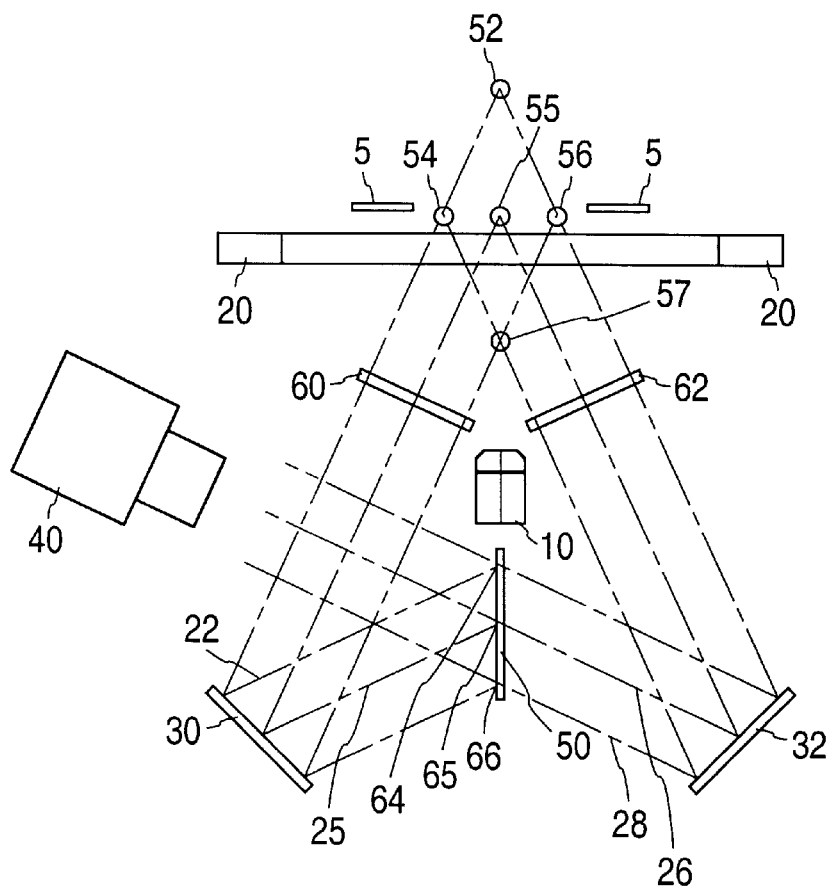
FIG. 2 shows a simplified schematic diagram of the inspection apparatus of FIG. 1, illustrating the principals by which the pertinent spatial coordinates of the grid array are measured.

FIG. 2 illustrates in detail how the spatial coordinates of the grid array 410 may be calculated using at least two of the plurality of oblique images captured by camera 40. In the example of FIG. 2, a left oblique image and a right oblique image are used to calculate the spatial coordinates of connectors on the grid array.

Referring to FIG. 2, points 54, 55, and 56 in the diagram represent three connectors of the grid array, and points 52 and 57 represent two imaginary points above and below the height of the grid array base plane, respectively. It is to be noted that for purposes of simplification, the explanation provided below with reference to FIG. 2 illustrates only a portion of a grid array which is actually inspected.

Figure 5:
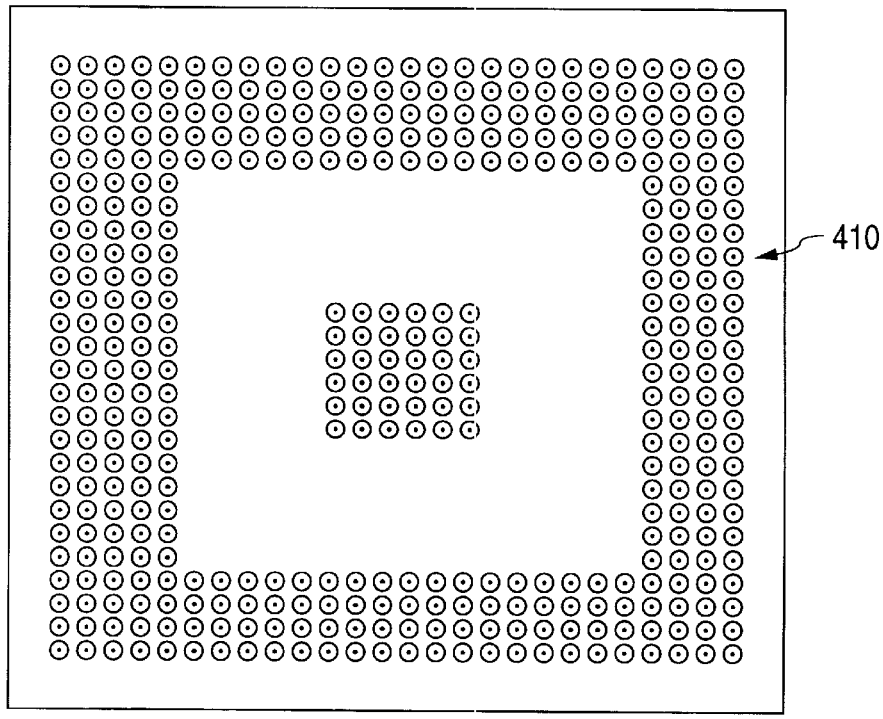
FIG. 5 shows an actual captured image of an alternate type of ball grid array package.

As illustrated in FIGS. 4 and 5, the illumination of the grid array by ring light source 20 creates small dark spots on the distal end portions of points 54, 55 and 56, which are located inside a bright circular background. Points 52 and 57 of FIG. 2 are imaginary object points included in the diagram for illustration purposes. When electronic light shutters 60 and 62 are open, an image point 65, for example, is formed on the beam splitter plate 50 by light ray 25. Image point 65 corresponds to connector point 55 in the grid array. Light ray 25 originates at point 55 in the grid array, passing through the electronic light shutter 60, and is reflected by mirror 30 to the beam splitter plate 50. A second superimposed image point 65 is formed by light ray 26, which originates from connector point 55. Light ray 26 travels from connector point 55, passing through electronic light shutter 62, and is reflected by mirror 32 onto the beam splitter 50. In the diagram of FIG. 2, point 55 and point 65 lie in a parallel virtual plane which transects both the beam splitter and connector point 55. This virtual plane corresponds to the unique optical reference plane of the optical system of the present invention, as described above. More specifically, the system is aligned so that point 55 at the grid array center will produce an image point 65 in the center of the camera viewing frame on beam splitter 50.

Next, consider connector point 54, which is located at the same relative height as point 55 in FIG. 2. Point 54 has an associated light ray 22, which passes through shutter 60 and is reflected by mirror 30 to form an image point 64 on beam splitter plate 50. Similarly, point 54 has an additional associated light ray 28, which passes through shutter 62, and is reflected by mirror 32 to form an image point 66 at the beam splitter 50. In the same manner, connector point 56 has associated image points 64 and 66 at beam splitter plate 50. Similarly, imaginary object point 52 has two image points which are both superimposed at point 64 on the beam splitter plate 50. Imaginary object point 57 also has two associated image points which are superimposed at point 66 on the beam splitter plate 50. By assigning a single X,Y coordinate system to the image points on the beam splitter, each of the plurality of oblique images superimposed on the beam splitter and captured by the camera device are directly mappable to the assigned X,Y coordinate system. Then, by using the assigned X,Y coordinate values of the various image points of each image, the representative spatial coordinates X,Y,Z of the object points 52, 54, 55, 56, and 57 may be computed as illustrated, for example, in FIG. 3.

One of the benefits of the technique of the present invention is that the configuration of the inspection apparatus 100 as shown, for example, in FIG. 1, allows each of the oblique images of the grid array to be mapped to a single X, Y coordinate system on beam splitter plate 50. In this manner, each of the oblique images captured by the image capturing device from beam splitter plate 50 are directly mappable to a single coordinate system, which, as explained in greater detail below, permits the technique of the present invention to compute the representative spatial coordinates X, Y, Z of the associated connector points of the grid array.

The technique of providing a plurality of different oblique images of the grid array which are each mappable to a common, single coordinate system is a unique and novel feature of the present invention. Moreover, the technique of using at least two differing oblique images of the grid array to compute the representative spatial coordinates of the connectors and other desired points of the grid array is also a unique and novel feature within the field of lead inspection systems. This latter technique is accomplished primarily due to the fact that each of the plurality of oblique images is mappable to a single coordinate system.

Conventionally, lead inspection systems which rely on camera images to determine coplanarity or spatial coordinates of the grid array have traditionally used techniques other than the technique of the present invention. For example, U.S. Pat. No. 5,621,530 to Marrable, Jr. describes a technique for verifying the coplanarity of a ball grid array wherein a camera is used to determine a focal length needed to precisely focus on each of the solder balls in the grid array. The coplanarity of the ball grid array may then be determined from the focus data. The technique of using of at least two oblique images of the grid array to compute the spatial coordinates and coplanarity values of the connectors in the grid array has traditionally been considered undesirable due, in part, to the massive amount of time and computational power required to compute the desired coordinate values from image points which were not directly mappable to a single coordinate system.

Figure 6:
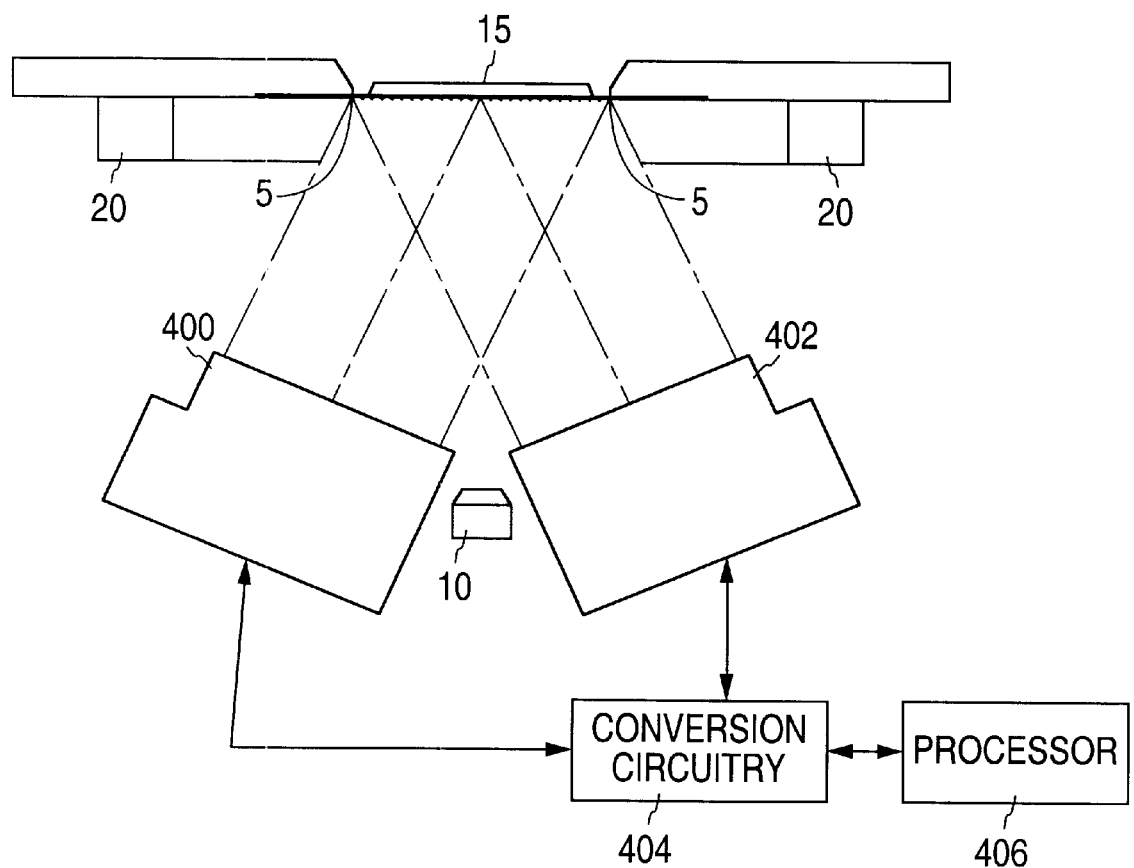
FIG. 6 shows a schematic diagram illustrating an alternate embodiment of the inspection apparatus of the present invention.

For example, FIG. 6 shows an alternate embodiment to the present invention wherein at least two image capturing devices 400 and 402 are used to capture a plurality of oblique images of the grid array of BGA package 15. One of the primary differences between the embodiment of FIG. 6 and the embodiment of FIG. 1 is that the left and right oblique images captured by cameras 400 and 402, respectively are not directly mappable to a single coordinate system. Therefore, the embodiment of FIG. 6 requires an additional conversion circuit 404, which converts the image points of each corresponding oblique image to a matrix array or vector array, which is then further converted using mathematical algorithms to enable each image to be mapped to a single coordinate system. After the oblique images have been converted mathematically to correspond to a single coordinate system, the spatial coordinates and coplanarity parameters of the grid array may then be computed by processor 420.

However, the use of at least two image capturing devices, and the inclusion of a conversion circuit 404 increases the cost, bulk, and complexity of the inspection apparatus. Moreover, a great deal of computational power is required by the conversion circuit to convert each of the oblique images to corresponding images which are mappable to a single coordinate system. In addition to the bulk and cost required to achieve such computational power, such computations require an extended amount of time to complete, thereby significantly increasing the amount of time needed to inspect each BGA package, which is also undesirable.

Figure 3:
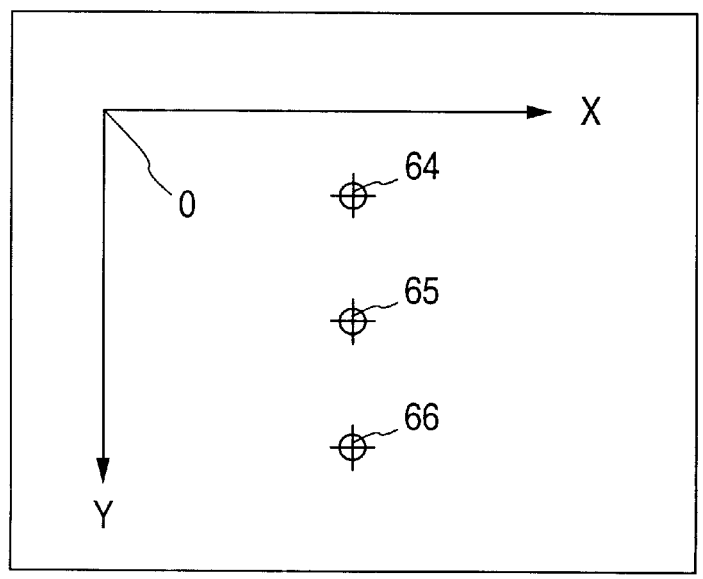
FIG. 3 is a schematic of a two-dimension coordinate frame for illustrating the principals by which the spatial coordinates of the grid array are derived from images captured by camera 40 of FIG. 2.

FIG. 3 illustrates the relative positions of image points 64, 65, and 66 on the beam splitter arbitrarily embedded into a two-dimensional X, Y coordinate frame. Since the image of FIG. 3 is captured in the form of a digital image frame, the units of the coordinates may be in, for example, pixel units. However, it is to be understood that other units of measurement may be used, as well as analog image frame data, so long as the image points within each captured image may be used to calculate the representative spatial coordinate values and coplanarity parameters of the connectors in the grid array 15. However, it is preferred to use a digital image frame and, in order to obtain higher accuracy in the measurement, sub-pixel image processing methods may be employed.

The X=0 and Y=0 of the digital image frame is represented by point 0 in the diagram. The coordinates of image points 64, 65, 66 are X(64) Y(64), X(65) Y(65) and X(66) Y(66), respectively. The representative height or Z coordinate of the object points 52, 54, 55, 56, 57 in FIG. 2 may be derived from the 2-Dimension coordinates of their associated image points 64, 65 and 66 in FIG. 3 as illustrated below:

(1) Object point 55 has left associated image point 65, and a right associated image point 65. The dual associated images superimpose at the same point 65 on beam splitter plate 50. The representative spatial coordinates x(55), y(55) and z(55) of point 55 are:

x(55)=X(65),
y(55)=Y(65),
z(55)={Y(65)+Y(65)}/2=Y(65).

(2) Object point 54 has left associated image point 64, and a right associated image point 66. The representative spatial coordinates x(54), y(54) and z(54) of point 54 are:

x(54)=X(64),
y(54)=Y(64), using the left associated image instead of right associated image as a convention, we arrive at:

z(54)={Y(64)+Y(66))}/2=Y(65).

Note that it is possible to calculate the value of z(54) using the above computation technique of the present invention because each of the associated image points (e.g. left image point 64 and right image point 66) are mappable to a single, common X,Y coordinate system.

(3) Object point 56 has left associated image point 66, and a right associated image point 64. The representative spatial coordinates x(56), y(56) and z(56) of point 56 are:

x(56)–X(66),
y(54)=Y(66),
z(56)={Y(66)+Y(64))}/2=Y(65).

(4) Object point 52 has left associated image point 64, an a right associated image point 64. The representative spatial coordinates x(52), y(52) and z(52) of point 52 are:

x(52)=X(64),
y(52)=Y(64),
z(52)={Y(64)+Y(64)}/2=Y(64).

(5) Object point 57 has left associated image point 66, right associated image point 66. The representative spatial coordinates x(57), y(57) and z(57) of point 57 are:

x(57)=X(66),
y(57)=Y(66),
z(57)={Y(66)+Y(66)}/2=Y(66).

FIG. 3 and FIG. 2 together illustrate how the technique present invention can be used to calculate and measure the coplanarity values and spatial coordinates of connectors of a grid array, particularly a ball grid array or other class of surface mount devices called SMT devices. The computed values of x,y,z are relative values, which may be converted into absolute length readings by correlating with measurements made on prior calibrated units or specially designed calibrators.

In order to determine coplanarity, the height data of all the connectors is first determined. The computed Z spatial coordinate is used to determine ball height for coplanarity, and the computed X and Y coordinates are used to determine the deviation from the true or specified position of the individual ball connectors. Next, for example, the least-mean-squared (LMS) plane which fits the spatial points (X, Y, Z) representing heights of the ball connectors is computed. A parallel shift of the LMS surface is made until it is tangential to the highest ball connector. This is the reference plane for coplanarity measurement. The difference in height between the reference plane and the individual ball will be the coplanarity measured value of each ball connector. Once a tolerance is set, for example 4 mil or $\frac{4}{1000}$ inch, measured coplanarity values for each ball connector must be less than the 4 mil tolerance. It is to be noted that other methods or techniques commonly know to one skilled in the art for determining the coplanarity reference plane may be employed where desirable.

FIG. 4 shows an actual captured image of one type of BGA package 450, showing the plurality of external lead connectors 410 and centered laser reference point 420. FIG. 4 shows one package model with epoxy encapsulation at the center portion of the device. This forms a small 'plateau' higher than surrounding substrate on which the ball connectors are mounted. If the height of this 'plateau' is greater than heights of the ball connectors, then the device cannot be surface mounted and soldered onto a printed circuit board. One use of the laser spot, therefore, is to determine the height of the 'plateau' and make sure that it is lower than the ball heights. FIG. 5 shows another package model where there is no epoxy encapsulation in the center portion.

As show in FIG. 4, the connectors of the grid array 410 are mounted on a substrate surface 415 of the electronic package 450. Within the perimeter of the ball grid array of package 450 is a raised center portion of substrate. A laser reference point 420 illuminates a center portion of the substrate so that the spatial coordinates and coplanarity value of the raised center substrate portion may be determined. The relative height of the substrate portion located at laser reference 420 may be calculated according to the above described technique of the present invention. The calculated relative height of the laser reference point may then be converted to an absolute height and compared against the height of each solder ball and the grid array. The height of each solder ball must, at a minimum, be greater than the height of the substrate portion located at reference point 420, otherwise faulty connections may result when the electronic package is connected to an external electronic component.

Thus, one function of the laser device 10 (FIG. 1) is to enable spatial coordinate measurement and comparison of a point illuminated by the laser relative to any connector of the grid array. Without providing a laser reference point as shown in FIG. 4, it would be extremely difficult to determine the height of the central substrate portion using the technique of the present invention due primarily to the lack of any illuminated reference point on the substrate. Therefore, the use of the laser device in conjunction with the technique of the present invention allows the spatial coordinates of any selected point on the base of the electronic package to be measured and calculated. It is also to be noted that the laser device may be replaced by alternative light sources adapted to project an illuminated spot or a plurality of illuminated spots onto the substrate portion to determine the heights of the corresponding projected spot positions.

Although several preferred embodiments of this invention have been described in detail herein with reference to the accompanying drawings, it is to be understood that the invention is not limited to these precise embodiments, and at various changes and modifications may be effected therein by one skilled in the art without departing from the scope of spirit of the invention as defined in the appended claims.

What is claimed is:

1. An inspection apparatus for an electronic package having a grid array of connectors mounted on a substrate, said connectors being used for external lead connection of the electronic package, said apparatus comprising:

an image capturing device;

an imaging system for providing a plurality of images of the grid array to said image capturing device:

each of said plurality of images corresponding to a different perspective view of said grid array;

each of said plurality of images further being mappable to a single coordinate system, at least two of the plurality of images being superimposed to determine spatial coordinates of at least a point in an imaged grid array.

2. The apparatus of claim 1 wherein said imaging system includes:
   image directing devices for simultaneously directing to said image capturing device said plurality of images; and
   shutters for providing a selected one of said plurality of images to said image capturing device at a given time.

3. The apparatus of claim 2 wherein said image directing devices includes a beam splitter having a partially reflective surface, said beam splitter being interposed along a light path of said one selected image between said shutters and said image capturing device.

4. The apparatus of claim 3 wherein said image directing devices further comprises at least two reflective devices including a first reflective device and a second reflective device;
   wherein each reflective device directs a different perspective view of said grid array to said beam splitter.

5. The apparatus of claim 4, wherein said plurality of images includes a first image defining a first light path, and a second image defining a second light path;
   said first image corresponding to a different perspective view of said grid array than said second image;
   said first light path being reflected by said beam splitter to said image capturing device;
   said second light path passing through said beam splitter to said image capturing device.

6. The apparatus of claim 5 wherein said beam splitter includes a longitudinal axis and a latitudinal axis which together define a plane;
   and wherein said first and second reflective devices are located on opposite sides of said plane.

7. The apparatus of claim 5, wherein said first image is captured by said image capturing device as a first captured image;
   and wherein said second image is captured by said image capturing device as a second captured image;
   and wherein said first and second captured images are each mappable to a single X,Y coordinate system for describing relative positions of each connector within each captured image.

8. The apparatus of claim 5 wherein said first image is a left oblique image of said grid array; and
   wherein said second image is a right oblique image of said grid array.

9. The apparatus of claim 4 wherein said reflective devices include mirrors or prisms.

10. The apparatus of claim 2 wherein said shutters includes:
    a plurality of shutters, each of said shutters being adapted to receive a light path representing a respective image from said plurality of images;
    each of said shutters having an open state for passing the light path of said respective image on to said image capturing device;
    each of said shutters further having a closed state for preventing the light path of said respective image from being passed on to said image capturing device; and
    a controller circuit connected to each of said shutters for coordinating control of each shutter such that, while a selected shutter of said plurality of shutters is open, the other shutters of said plurality of shutters are closed, thereby providing a single image of said plurality of images to said image capturing device at a given time.

11. The apparatus of claim 10 wherein each of said plurality of shutters is an electronic light shutter.

12. The apparatus of claim 1 further including a computer system adapted to receive each of said plurality of images captured by said image capturing device for using at least two of a plurality of captured images to calculate spatial coordinate values of each connector of the grid array;
    wherein said plurality of captured images includes a first captured image and a second captured image; and
    wherein said computer system includes an assigning subsystem for assigning to said first and second captured images a single coordinate system for describing relative positions of points within each captured image.

13. The apparatus of claim 12 wherein said at least two of said plurality of captured images include a left oblique image of said grid array and a right oblique image of said grid array.

14. The apparatus of claim 12 wherein said computer system further calculates the spatial coordinates of a distal end portion of each connector of the grid array.

15. The apparatus of claim 12 further including a laser for providing an illuminated reference point on a portion of said substrate, wherein said computer system is further adapted to utilize said reference point to calculate spatial coordinates of said substrate portion.

16. The apparatus of claim 15 wherein said laser comprises a self focussing laser diode.

17. The apparatus of claim 15 wherein the computer system further includes a comparing subsystem for comparing said calculated spatial coordinate values with predetermined values to determine whether the electronic package meets acceptable manufacturing standards, and
    wherein said comparing subsystem is configured or designed to compare the spatial coordinate values of said substrate portion to the spatial coordinate values of each of said connectors to determine whether physical parameters of each connector fall within acceptable parameters as determined by the spatial coordinates of the substrate portion.

18. The apparatus of claim 17 wherein said illuminated reference point is located at a center portion of the electronic package.

19. The apparatus of claim 1 further including an illumination device for illuminating said grid array.

20. The apparatus of claim 19 wherein said illumination device comprises a ringed light source.

21. The apparatus of claim 1 wherein said image capturing device comprises a CCD camera.

22. An inspection apparatus for an electronic package having a grid array of connectors mounted on a substrate, said connectors being used for external lead connection of the electronic package, said apparatus comprising:
    an image capturing device;
    a beam splitter having a partially reflective surface and having a longitudinal and a latitudinal axis which together define a plane;
    at least two image reflecting devices, including a first reflecting device and a second reflecting device;
    said first and second reflecting devices being located on opposite sides of said plane, said first reflecting device directing a first oblique image of said grid array to said image capturing device via said beam splitter, said first oblique image corresponding to a first perspective view of said grid array;
    said second reflecting device directing a second oblique image of said grid array to said image capturing device via said beam splitter, said second oblique image corresponding to a second perspective view of said grid array different from that of said first perspective view;

wherein said first and second oblique images are mappable to a single coordinate system, and further wherein the first and second oblique images are superimposed to determine spatial coordinates of at least a point in an imaged grid array.

23. The apparatus of claim 22 wherein a light path of said first oblique image is reflected by said beam splitter and is received by said image capturing device as a first captured image, and wherein a light path of said second oblique image passes through said beam splitter and is received by said image capturing device as a second captured image, and wherein said first and second captured images are directly mappable to a single coordinate system.

24. The apparatus of claim 22 further comprising:
a plurality of shutters including a first shutter and a second shutter, said first shutter being interposed along an optical path of said first oblique image between said grid array and said beam splitter, said second shutter being interposed along an optical path of said second oblique image between said grid array and said beam splitter; and
a control circuit connected to each of said shutters for simultaneously coordinating control of each shutter such that, while a selected shutter of said plurality of shutters is open, the non-selected shutters of said plurality of shutters are closed, thereby providing a desired image to said image capturing device at a given time.

25. The apparatus of claim 22 wherein said first oblique image is a left oblique image of said grid array, and said second oblique image is a right oblique image of said grid array.

26. The apparatus of claim 24 wherein the first shutter is interposed between the grid array and the first reflecting device.

27. The apparatus of claim 24 wherein the first shutter is interposed between the first reflecting device and the beam splitter.

28. The apparatus of claim 22 wherein said reflecting devices include mirrors or prisms.

29. The apparatus of claim 24 wherein each of said plurality of shutters is an electronic light shutter.

30. The apparatus of claim 22 further including a computer system adapted to receive each of a plurality of images captured by said image capturing device for using at least two of the plurality of captured images to calculate spatial coordinate values of each connector of the grid array.

31. The apparatus of claim 30 further including a laser for providing an illuminated reference point on a portion of said substrate, wherein said computer system is further adapted to utilize said reference point to calculate spatial coordinates of said substrate portion.

32. The apparatus of claim 31 wherein the computer system further includes a comparing subsystem for comparing said calculated spatial coordinate values with predetermined values to determine whether the electronic package meets acceptable manufacturing standards, and
wherein said comparing subsystem is configured or designed to compare the spatial coordinate values of said substrate portion to the spatial coordinate values of each of said connectors to determine whether physical parameters of each connector fall within acceptable parameters as determined by the spatial coordinates of the substrate portion.

33. The apparatus of claim 32 wherein said illuminated reference point is located at a center portion of the electronic package.

34. An inspection apparatus for an electronic package having a grid array of connectors mounted on a substrate, said connectors being used for external lead connection of the electronic package, said apparatus comprising:
a plurality of image capturing devices, including a first image capturing device and a second image capturing device, said first image capturing device positioned to capture a first image of said grid array from a first perspective, said second image capturing device positioned to capture a second image of said grid array from a second perspective different from said first perspective;
an imaging system for converting said first image and said second image to respective images which are each mappable to a single coordinate system; and
a computer system adapted to receive each converted image from said imaging system for using at least two of a plurality of captured images to calculate spatial coordinate values of each connector of the grid array, the at least two captured images being superimposed to determine the spatial coordinate values of each connector.

35. The apparatus of claim 34 further including a laser for providing an illuminated reference point on a portion of said substrate, wherein said computer system is further adapted to utilize said reference point to calculate spatial coordinates of said substrate portion.

36. The apparatus of claim 35 wherein the computer system further includes comparing subsystem for comparing said calculated spatial coordinate values with predetermined values to determine whether the electronic package meets acceptable manufacturing standards, and
wherein said comparing subsystem is configured or designed to compare the spatial coordinate values of said substrate portion to the spatial coordinate values of each of said connectors to determine whether physical parameters of each connector fall within acceptable parameters as determined by the spatial coordinates of the substrate portion.

37. The apparatus of claim 34 wherein at least one image capturing device includes a CCD camera.

38. In a system for inspecting a grid array of external lead connectors mounted on a substrate of an electronic package, the system including an image capturing device, a method for computing spatial coordinate values of each connector, said method comprising:
(a) providing to the image capturing device a first oblique image of the grid array, said first oblique image including a first plurality of image points corresponding to the external lead. connectors of the grid array;
(b) assigning to said first oblique image an X, Y coordinate system for describing relative positions of said image points;
(c) providing to the image capturing device a second oblique image of the grid array, said second oblique image including a second plurality of image points corresponding to the external lead connectors of the grid array, said second oblique image being different than said first oblique image;
(d) assigning to said second oblique image said X, Y coordinate system;
(e) superimposing said first oblique image and said second oblique image; and
(f) using X, Y coordinate values of said first and second plurality of image points from said superimposed first and second oblique images to compute representative spatial coordinates X, Y, Z of each connector of the grid array.

39. The method of claim 37 wherein said first oblique image is a left oblique image of said array, and said second oblique image is a right oblique image of said array.

40. The method of claim 37, wherein said providing step (a) includes directing said first oblique image to a partially reflective beam splitter, and wherein said providing step (c) includes directing said second oblique image to said beam splitter.

41. The method of claim 40 further including:
using a first reflecting device to direct said first oblique image to the beam splitter; and
using a second reflecting device to direct said second oblique image to the beam splitter.

42. The method of claim 41 further including using said image capturing device to capture said first and second oblique images from said beam splitter.

43. The method of claim 42 further including:
using at least one shutter to selectively provide to said image capturing device a single selected image; and
capturing said single selected image during a specific time interval using said image capturing device.

44. The method of claim 43 further including:
using a first shutter to block a light path of said first oblique image while said image capturing device is capturing said second oblique image; and
using a second shutter to block a light path of said second oblique image while said image capturing device is capturing said first oblique image.

45. A method for inspecting a grid array of external lead connectors mounted on a substrate of an electronic package, said method comprising:
(a) providing a plurality of images of the grid array to an image capturing device, each of said plurality of images corresponding to a different perspective view of said array, each of said plurality of images further being mappable to a single coordinate system;
(b) using at least two of said plurality of captured images to calculate spatial coordinate values of each connector of the grid array by superimposing at least the two captured images; and
(c) comparing said calculated spatial coordinate values with predetermined values to determine whether the electronic package meets acceptable manufacturing standards.

46. The method of claim 45, wherein said providing step (a) includes directing said each of said plurality of images to a partially reflective beam splitter.

47. The method of claim 46 further including using said image capturing device to capture each of the plurality of images from said beam splitter.

48. The method of claim 45 further including:
projecting a laser beam onto a portion of said substrate to establish a reference point;
using said reference point to calculate a reference value relating to a minimum permissible height for each connector of the grid array.

49. The method of claim 48 further including:
converting pertinent parameters of the spatial coordinate values of each connector to absolute length readings, wherein said absolute length readings include a value relating to a height of each connector; and
comparing the height value of each connector to said reference value to determine whether each connector falls within acceptable physical parameters.

50. The method of claim 46 further including:
using at least one shutter to selectively provide to said image capturing device a selected image of said plurality of images; and
capturing said selected image during a specific time interval using said image capturing device.

51. The method of claim 50 further including:
using a first shutter to block a light path of a first image while said image capturing device is capturing a second image; and
using a second shutter to block a light path of a second oblique image while said image capturing device is capturing a first oblique image.

52. The method of claim 51 wherein said first oblique image is a left oblique image of said array, and said second oblique image is a right oblique image of said array.

53. A method for inspecting a grid array of external lead connectors mounted on a substrate of an electronic package, said method comprising:
(a) providing to an image capturing device a first oblique image of the grid array, said first oblique image including a first plurality of image points corresponding to the external lead connectors of the grid array;
(b) mapping said first oblique image an X, Y coordinate system;
(c) providing to the image capturing device a second oblique image of the grid array, said second oblique image including a second plurality of image points corresponding to the external lead connectors of the grid array, said second oblique image being different than said first oblique image;
(d) mapping said second oblique image to said X, Y coordinate system;
(e) superimposing said first and second oblique images;
(f) using X, Y coordinate values of said first and second plurality of image points from said superimposed first and second oblique images to compute representative spatial (X, Y, Z) coordinate values of each connector of the grid array; and
(g) comparing said computed spatial coordinate values with predetermined values to determine whether the electronic package meets acceptable manufacturing standards.

54. The method of claim 53, wherein said providing step (a) includes directing said first oblique image to a partially reflective beam splitter, and wherein said providing step (c) includes directing said second oblique image to said beam splitter.

55. The method of claim 54 further including:
using a first reflecting device to direct said first oblique image to the beam splitter; and
using a second reflecting device to direct said second oblique image to the beam splitter.

56. The method of claim 55 further including using said image capturing device to capture said first and second oblique images from said beam splitter.

57. The method of claim 53 further including:
projecting a laser beam onto a portion of said substrate to establish a reference point;
using said reference point to calculate a reference value relating to a minimum permissible height for each connector of the grid array.

58. The method of claim 57 further including:
converting pertinent parameters of the computed spatial coordinate values of each connector to absolute length readings, wherein said absolute length readings include a value relating to a height of each connector; and comparing the height value of each connector to said reference value to determine whether each connector falls within acceptable physical parameters.

59. The method of claim 55 further including:

using at least one shutter to selectively provide to said image capturing device a selected image of said first and second oblique images; and capturing said selected image during a specific time interval using said image capturing device.

60. The method of claim 59 further including:

using a first shutter to block a light path of said first oblique image while said image capturing device is capturing said second oblique image; and using a second shutter to block a light path of said second oblique image while said image capturing device is capturing said first oblique image.

61. The method of claim 60 wherein said first oblique image is a left oblique image of said array, and said second oblique image is a right oblique image of said array.

* * * * *